(12) United States Patent
Lamanna et al.

(10) Patent No.: US 11,858,875 B2
(45) Date of Patent: Jan. 2, 2024

(54) PROPENYLAMINES AND METHODS OF MAKING AND USING SAME

(71) Applicant: 3M INNOVATIVE PROPERTIES COMPANY, St. Paul, MN (US)

(72) Inventors: William M. Lamanna, Stillwater, MN (US); Michael J. Bulinski, Stillwater, MN (US); Sean M. Smith, Woodbury, MN (US); Alexandre R. Monteil, St. Paul, MN (US); Michael G. Costello, Afton, MN (US); John G. Owens, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 17/874,851

(22) Filed: Jul. 27, 2022

(65) Prior Publication Data

US 2022/0380296 A1    Dec. 1, 2022

Related U.S. Application Data

(62) Division of application No. 16/326,464, filed as application No. PCT/US2017/047720 on Aug. 21, 2017, now Pat. No. 11,479,525.

(60) Provisional application No. 62/377,879, filed on Aug. 22, 2016.

(51) Int. Cl.
| | |
|---|---|
| *C07C 209/68* | (2006.01) |
| *C07D 295/067* | (2006.01) |
| *C09K 5/10* | (2006.01) |
| *H01M 8/04029* | (2016.01) |
| *H01M 8/04701* | (2016.01) |
| *H05K 7/20* | (2006.01) |

(52) U.S. Cl.
CPC ........ *C07C 209/68* (2013.01); *C07D 295/067* (2013.01); *C09K 5/10* (2013.01); *H01M 8/04029* (2013.01); *H01M 8/04701* (2013.01); *H05K 7/20218* (2013.01)

(58) Field of Classification Search
CPC .................................................. C07C 209/68
See application file for complete search history.

(56) References Cited

U.S. PATENT DOCUMENTS

| | | |
|---|---|---|
| 3,000,979 A | 9/1961 | Gibbs et al. |
| 4,985,556 A | 1/1991 | Abe et al. |
| 6,203,944 B1 | 3/2001 | Turner et al. |
| 6,883,908 B2 | 4/2005 | Young et al. |
| 7,297,400 B2 | 11/2007 | Yang et al. |
| 7,411,095 B2 * | 8/2008 | Okazaki ............... C07D 285/14 564/478 |
| 7,691,437 B2 | 4/2010 | Ellis et al. |
| 7,767,728 B2 | 8/2010 | Lu et al. |
| 7,947,376 B2 | 5/2011 | Sherman et al. |
| 8,236,429 B2 | 8/2012 | Sherman et al. |
| 8,361,632 B2 | 1/2013 | Everaerts et al. |
| 8,361,633 B2 | 1/2013 | Everaerts et al. |
| 9,309,443 B2 | 4/2016 | Yurt et al. |
| 9,957,428 B2 | 5/2018 | Bulinski et al. |
| 10,266,472 B2 | 4/2019 | Bulinski et al. |
| 10,557,069 B2 | 2/2020 | Bulinski et al. |
| 10,738,001 B2 | 8/2020 | Lamanna et al. |
| 2009/0280322 A1 | 11/2009 | Daniels et al. |
| 2010/0139274 A1 | 6/2010 | Zyhowski et al. |
| 2011/0144399 A1 | 6/2011 | Elomari et al. |
| 2011/0215273 A1 | 9/2011 | Uenveren et al. |
| 2013/0091843 A1 | 4/2013 | Zyhowski et al. |
| 2013/0136874 A1 | 5/2013 | Xia et al. |
| 2014/0171698 A1 | 6/2014 | Elsheikh et al. |
| 2015/0083979 A1 | 3/2015 | Costello et al. |
| 2015/0231621 A1 | 8/2015 | Grotjahn et al. |

(Continued)

FOREIGN PATENT DOCUMENTS

| | | |
|---|---|---|
| JP | 01070445 A | 3/1989 |
| WO | 2000003444 A1 | 1/2000 |

(Continued)

OTHER PUBLICATIONS

1507 Extended EP Search Report for EP17844197.8, PCT/US2017/047720 dated Nov. 22, 2019, 7 pages.

Belen'Kii, "Electrophilic Isomerization of Fluoro-Containing Olefins", Institute of Heteroorganic Compounds, Academy of Sciences of the USSR, Moscow. Translated from Izvestiya Akademii Nauk SSSR, Seriya Khimicheskaya, Jul. 1978, No. 7, pp. 1640-1643.

Ellis, Cleaning and Contamination of Electronics Components and Assemblies, 182-94 (1986).

(Continued)

*Primary Examiner* — Amanda C. Walke
(74) *Attorney, Agent, or Firm* — Jeffrey M. Olofso

(57) ABSTRACT

A composition includes a perfluorinated propenylamine represented by the following general formula (1):

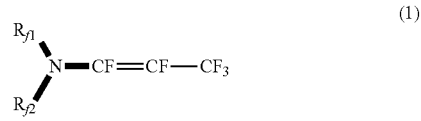

(1)

Each occurrence of $R_{f1}$ and $R_{f2}$ is:
(i) independently a linear or branched perfluoroalkyl group having 1-8 carbon atoms and optionally comprises one or more catenated heteroatoms; or
(ii) bonded together to form a ring structure having 4-8 carbon atoms and that optionally comprises one or more catenated heteroatoms.

At least 60 wt. % of the perfluorinated propenylamine is in the form of the E isomer, based on the total weight of the perfluorinated propenylamine in the composition.

3 Claims, No Drawings

(56) References Cited

U.S. PATENT DOCUMENTS

| | | |
|---|---|---|
| 2015/0284601 A1 | 10/2015 | Yurt et al. |
| 2016/0145195 A1 | 5/2016 | Bulinski et al. |
| 2016/0289515 A1 | 10/2016 | Clapper et al. |
| 2017/0369755 A1 | 12/2017 | Zhang |

FOREIGN PATENT DOCUMENTS

| | | |
|---|---|---|
| WO | 2011112508 A1 | 9/2011 |
| WO | 2011119388 A2 | 9/2011 |
| WO | 2013151741 A1 | 10/2013 |
| WO | 2013161812 A1 | 10/2013 |
| WO | 2014078115 A1 | 5/2014 |
| WO | 2015095285 A1 | 6/2015 |
| WO | 2015133517 A1 | 9/2015 |
| WO | 2016011220 A1 | 1/2016 |
| WO | 2016089805 A1 | 6/2016 |
| WO | 2016094113 A1 | 6/2016 |
| WO | 2016178871 A1 | 11/2016 |
| WO | 2019003138 A1 | 1/2019 |

OTHER PUBLICATIONS

Fleming, "Polyfluoroalkyl Derivatives Of Nitrogen. Part XLII. Reaction of N-Bromobistrifluoromethylamine With 1H-Pentafluoropropene and Some Further Studies on the Thermal Rearrangement of NN-Bistrifluoromethyl-Vinylamines", Journal Chemical Society, Pierkin Transactions 1, 1975, No. 17, pp. 1633-1638.
Hayakawa, "New per fluoropolymers bearing dialkylamino groups as side chains", Polymer, 1995, vol. 36, No. 14, pp. 2807-2812.
International Search Report for PCT International Application No. PCT/US2017/47720, dated Oct. 18, 2017, 2 pages.
Kaneko, "A New Synthetic Route to Perfluoroacrylic Acid", Reports Research Laboratory Asahi Glass Co., Ltd. 1986, vol. 36, No. 2, pp. 243-248.
Krespan, "The Chemistry of Highly Fluorinated Carbocations", Chemical Reviews, 1996, vol. 96, No. 8, pp. 3269-3301.
Newsholme, "Some further reactions of bis(trifluoromethyl)amino-oxyl with alkenes", Journal of Fluorine Chemistry, 1994, vol. 69, pp. 163-169.

\* cited by examiner

PROPENYLAMINES AND METHODS OF MAKING AND USING SAME

FIELD

The present disclosure relates to propenylamines and methods of making and using the same, and to working fluids that include the same.

BACKGROUND

Various propenylamine compounds are described in, for example, T. Abe, JP 01070444A; T. Abe, JP 0107445A; and M. Bulinski, WO 2015/095285.

SUMMARY

In some embodiments, a composition is provided. The composition includes a perfluorinated propenylamine represented by the following general formula (1):

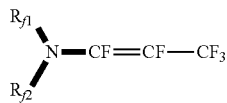

(1)

Each occurrence of $R_{f1}$ and $R_{f2}$ is:
(i) independently a linear or branched perfluoroalkyl group having 1-8 carbon atoms and optionally comprises one or more catenated heteroatoms; or
(ii) bonded together to form a ring structure having 4-8 carbon atoms and that optionally comprises one or more catenated heteroatoms; and At least 60 wt. % of the perfluorinated propenylamine is in the form of the E isomer, based on the total weight of the perfluorinated propenylamine in the composition.

In some embodiments, a method of making the above-described composition is provided. The method includes contacting a perfluorinated allylamine of general formula (2) with an active isomerization catalyst;

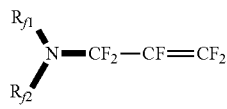

(2)

and carrying out a selective catalytic isomerization to form a 1-propenylamine of general formula (1);

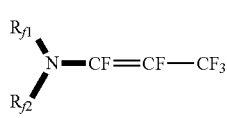

(1)

The selectivity for formation of the E isomer of formula (1) is at least 60% wt. %, based on the total weight of the propenylamine in the composition.

In some embodiments, a working fluid is provided. The working fluid includes the above-described composition. The above-described composition is present in the working fluid at an amount of at least 25% by weight, based on the total weight of the working fluid.

In some embodiments, an apparatus for heat transfer is provided. The apparatus includes a device; and a mechanism for transferring heat to or from the device. The mechanism includes a heat transfer fluid that includes the above-described composition or working fluid.

In some embodiments, a method of transferring heat is provided. The method includes providing a device; and transferring heat to or from the device using a heat transfer fluid that includes the above-described composition or working fluid.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

In view of an increasing demand for environmentally friendly and low toxicity chemical compounds, it is recognized that there exists an ongoing need for new working fluids that provide further reductions in environmental impact and toxicity, and which can meet the performance requirements (e.g., nonflammability, solvency, stability, and operating temperature range) of a variety of different applications (e.g., heat transfer, two-phase immersion cooling, foam blowing agents, solvent cleaning, deposition coating solvents, and electrolyte solvents and additives), and be manufactured cost-effectively.

Generally, the present disclosure relates to propenylamine compounds that include at least one catenary nitrogen atom and are highly enriched in the E (or trans) isomer. The present disclosure also describes high yield methods of making such E-enriched compounds. Surprisingly, it has been discovered that the E-enriched propenylamines have significantly shorter atmospheric lifetimes compared to the corresponding Z (or cis) isomers or an equilibrium mixture of E and Z isomers and, therefore, have correspondingly lower global warming potentials. The propenylamines of the present disclosure are also generally non-flammable, have zero ozone depletion potential, and provide low toxicity for safe handling.

As used herein, "catenated heteroatom" means an atom other than carbon (for example, oxygen, nitrogen, or sulfur) that is bonded to at least two carbon atoms in a carbon chain (linear or branched or within a ring) so as to form a carbon-heteroatom-carbon linkage.

As used herein, "fluoro-" (for example, in reference to a group or moiety, such as in the case of "fluoroalkylene" or "fluoroalkyl" or "fluorocarbon") or "fluorinated" means (i) partially fluorinated such that there is at least one carbon-bonded hydrogen atom, or (ii) perfluorinated.

As used herein, "perfluoro-" (for example, in reference to a group or moiety, such as in the case of "perfluoroalkylene" or "perfluoroalkyl" or "perfluorocarbon") or "perfluorinated" means completely fluorinated such that, except as may be otherwise indicated, there are no carbon-bonded hydrogen atoms replaceable with fluorine.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

In some embodiments, the present disclosure is directed to propenylamines of general formula (1).

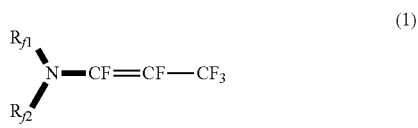

The propenylamines of general formula (1) can exist in one of two isomeric forms, the E or Z isomer, which are depicted below in general formulas (1A) and 1(B), respectively.

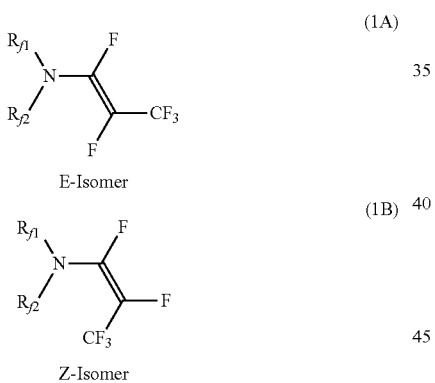

Surprisingly, it has been discovered that the E-isomer [general formula (1A)] has a significantly shorter atmospheric lifetime than the Z isomer [Structure (1B)], and correspondingly lower global warming potential (GWP). Therefore, it is advantageous, from an environmental sustainability standpoint, if the propenylamines could be enriched in the lower GWP E-isomer (thus reducing the average GWP of the mixture).

In some embodiments, the present disclosure is further directed to methods of making the above-described E-isomer enriched propenylamines of general formula (1). However, heretofore, this has not been possible, since all known methods of preparing such propenylamines lead to a mixture of E and Z isomers, with the thermodynamically more stable Z isomer generally present as the major isomer. Additionally, known processes designed to isomerize the E and Z isomers would tend to favor the thermodynamically more stable Z isomer. Still further, the boiling points of the E and Z isomers are typically very similar (within a few degrees C.

or less of each other), thus making separation by distillation either impossible or impractical for achieving any significant level of enrichment of the E isomer. The present disclosure provides a solution to this problem in that it broadly describes propenylamines that are highly enriched in the thermodynamically less stable E isomer and high yield methods for preparing such E-enriched mixtures without sacrificing overall yield and avoiding the need to dispose of the less desirable Z isomer.

In some embodiments, the present disclosure is directed to compositions that include the propenylamines of general formula (1), wherein at least 60 wt. %, 70% wt. %, 80 wt. %, 90 wt. %, 95 wt. % or 98 wt. % of the propenylamines are in the form of the E isomer (formula 1A) (the remainder being the Z isomer (formula 1B)), based on the total weight of the propenylamines of general formula (1) in the composition.

In illustrative embodiments, $R_{f1}$ and $R_{f2}$ in general formula (1) may be, independently, linear or branched perfluoroalkyl groups having 1-8 carbon atoms, 1-6 carbon atoms, or 1-4 carbon atoms. In further embodiments, $R_{f1}$ and $R_{f2}$ may be bonded together to form a ring structure having 4-8 carbon atoms, 4-6 carbon atoms, or 4 carbon atoms. Optionally, $R_{f1}$ and $R_{f2}$ may include one or more catenated heteroatoms. In some embodiments, if $R_{f1}$ and $R_{f2}$ are bonded together to form a ring structure that comprises a second nitrogen heteroatom, said second nitrogen heteroatom may be tertiary and may be bonded to a perfluoroalkyl group having 1-3 or 2-3 carbon atoms.

In various embodiments, representative examples of the compounds of general formula (1) include the following:

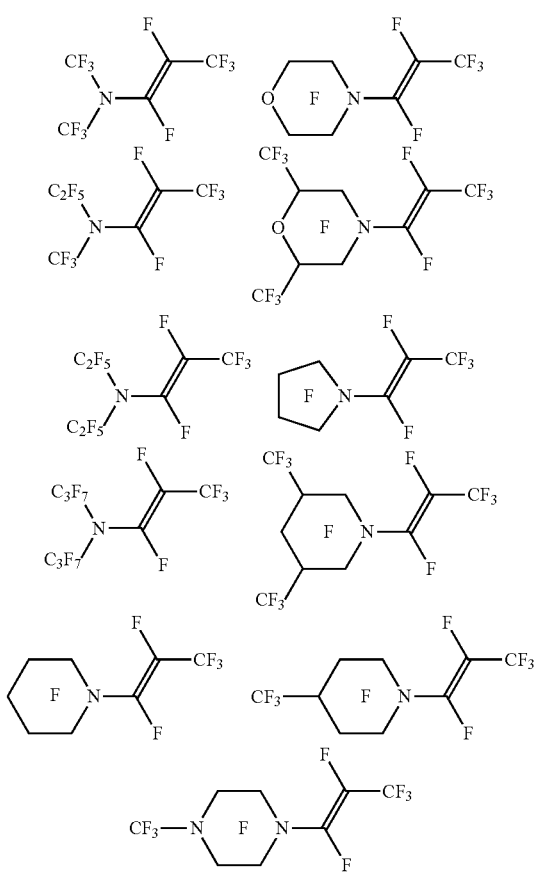

-continued

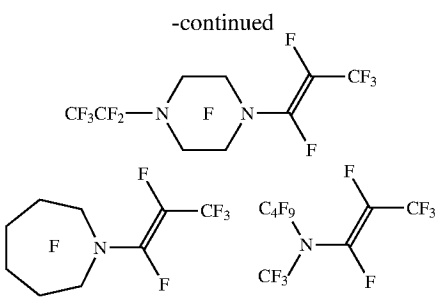

In some embodiments, the E isomer enriched propenylamine compounds of the present disclosure may be hydrophobic, relatively chemically unreactive, and thermally stable. As discussed above, the E isomer enriched propenylamine compounds may have a low environmental impact. In this regard, the E isomer enriched 1-propenylamine compounds may have a global warming potential (GWP, over 100 year ITH)) of less than 500, 300, 200, 100, 80, or less than 60. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{oi} e^{-t/\tau_i} dt}{\int_0^{ITH} a_{CO_2}[C_{CO_2}(t)]dt}$$

In this equation ad is the radiative forcing per unit mass increase of a compound in the atmosphere (the change in the flux of radiation through the atmosphere due to the IR absorbance of that compound), C is the atmospheric concentration of a compound, τ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

The perfluorinated propenyl amines of general formula (1) can be prepared by electrochemical perfluorination of the appropriate nitrogen containing hydrocarbon carboxylate derivatives followed by decarboxylation of the perfluorinated nitrogen-containing carboxylates, carbonyl fluorides, or esters using procedures that are well known in the art, including those described in T. Abe, JP 01070444A; T. Abe, JP 0107445A; or M. Bulinski, WO 2015/095285, which are herein incorporated by reference in their entirety. However, as discussed above, such methods yield a mixture of perfluorinated E- and Z 1-propenylamines in which the thermodynamically preferred Z isomer is the major component.

In some embodiments, the present disclosure is directed to high yield and selective methods of synthesizing the propenyl amines of general formula (1) that are enriched in the E isomer, without resorting to impractical separation methods and the cost and waste associated with disposal of the higher GWP Z isomer. In some embodiments, the method includes selectively isomerizing a perfluorinated allylamine of general formula (2) over an isomerization catalyst to predominantly form the E-1-propenylamine of general formula (1A), while avoiding significant formation of the thermodynamically more stable Z-1-propenylamine of general formula (1B).

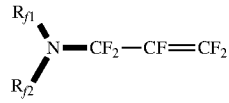

(2)

In some embodiments, the synthesis methods of the present disclosure may include a catalytic isomerization process which provides a mechanism for isomerizing a perfluorinated allylamine of general structure (2) to the corresponding E-1-propenylamine of general structure (1A) with a surprisingly high degree of selectivity. In some embodiments, the process may include catalytically isomerizing the terminal olefin of the perfluorinated allylamine to the corresponding internal olefin, with a surprisingly strong preference for the E (vs. Z) internal olefin isomer (even though the Z isomer is the thermodynamically more stable isomer).

In some embodiments, the catalytic isomerization process may be described by the reaction shown in Scheme 1, in which the E-1-propenyl amine is the major isomerization product and the Z-1-propenylamine is the minor isomerization product.

Scheme 1: Selective Catalytic Isomerization of Terminal Allylamine to Internal E-1-Propenyl Amine

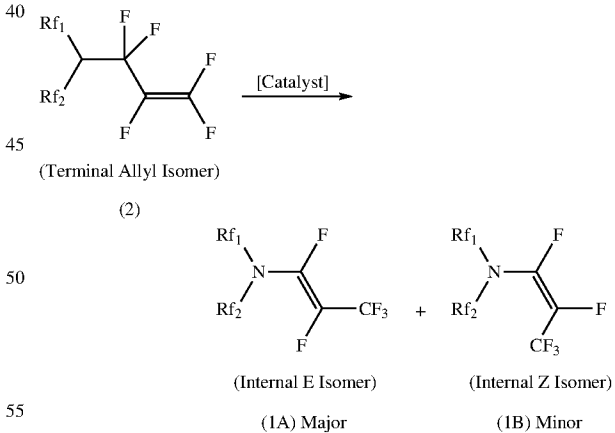

In some embodiments, catalysts for use in the catalytic isomerization process shown in Scheme 1 may include Lewis acidic metal fluorides and metalloid fluorides including, for example, any or all of $TiF_4$, $ZrF_4$, $NbF_5$, $TaF_5$, $BF_3$, $SbF_5$. In various embodiments, the catalyst may include any or all of $TiF_4$, $NbF_5$, $TaF_5$, and $SbF_5$. In some embodiments, the catalyst may include any or all of $NbF_5$ and $TaF_5$. In illustrative embodiments, in addition or as an alternative to the aforementioned catalysts, catalysts suitable for use in the methods of the present disclosure may include certain other fluorinated Lewis acids (including perfluorinated Lewis acids and certain Lewis acid mixed chlorofluorides), such as any or all of ACF (aluminum chlorofluoride), rare earth metal fluorides (including lanthanide and actinide metal fluorides), antimony chlorofluorides (including $SbCl_2F_3$ and $SbCl_4F$), as well as the Bronsted acid, $HSbF_6$. In other embodiments, the catalyst may include Lewis acidic metal chlorides and metalloid chlorides, including, for example, any or all of $AlCl_3$, $SbCl_5$, $TiCl_4$, and the like. It is believed that the latter Lewis acid catalysts form mixed chlorofluorides in situ via a halogen exchange reaction with the starting fluorinated allyl amine and it is these mixed chlorofluorides that are the active isomerization catalysts. Surprisingly, it was discovered that the Lewis acidic metal chlorides and metalloid chlorides are as effective as their fluoride counterparts, which is significant because the chlorides may be obtained at an appreciably lower materials cost. The Lewis acidic metal and metalloid fluorides, chlorofluorides, and chlorides useful as catalysts in the processes of the present disclosure may be chosen from groups 3 through 15 of the periodic table (modern IUPAC convention), including the lanthanide and actinides series. In one embodiment the catalysts are chosen from groups 4, 5, 13, and 15 of the periodic table.

In some embodiments, the reaction described in Scheme 1 may be carried out neat (i.e., in the absence of solvent), although inert solvents such as perfluorinated hydrocarbons may also be employed, if desired. Reaction temperature and reaction time may be selected based on the catalyst employed. For example, with some catalysts, low temperatures (e.g., ≤0° C.) and short reaction times (e.g., ~1 hr) may be employed, because at higher temperatures the catalyst will catalyze E/Z isomerization, thus resulting in a loss of selectivity. As an additional example, reaction temperatures between 20-100° C. and higher may be employed to increase the rates of reaction such that the isomerization reaction is complete or nearly complete in a period of approximately 1-20 hours or less. When using the catalysts of the present disclosure, the catalytic isomerization process of Scheme 1 may proceed with negligible side reactions, thus no or relatively few (less than 5%, 3%, 2%, or 1% by weight) detectable side products are formed, which might otherwise contaminate the propenylamine product.

In some embodiments, the perfluorinated allylamines of general formula (2) may be prepared by methods that are well known in the art, including those methods described in T. Abe, JP 01070444A; and T. Abe, JP 0107445A, both of which are incorporated herein by reference in their entirety and described in Scheme 2 The first step consists of a Michael addition of a secondary amine $(R_H^1(R_H^2)NH)$ to methyl methacrylate. The respective beta-aminoesters undergo electrochemical fluorination to afford the desired perfluorinated acid fluoride intermediates which are subjected to thermolysis in the presence of $Na_2CO_3$ to give a mixture of perfluorinated allylic amines and perfluorinated 1-aminopropenes. The desired perfluorinated allyl amine products can be purified by distillation and have been used in pure form for fluoropolymer synthesis (Y. Hayakawa et al. Polymer 1995, 36, 2807) and for additions by bis(trifluoromethyl)amino-oxyl reagent (G. Newsholme et al. J. Fluorine Chem. 1994, 69, 163).

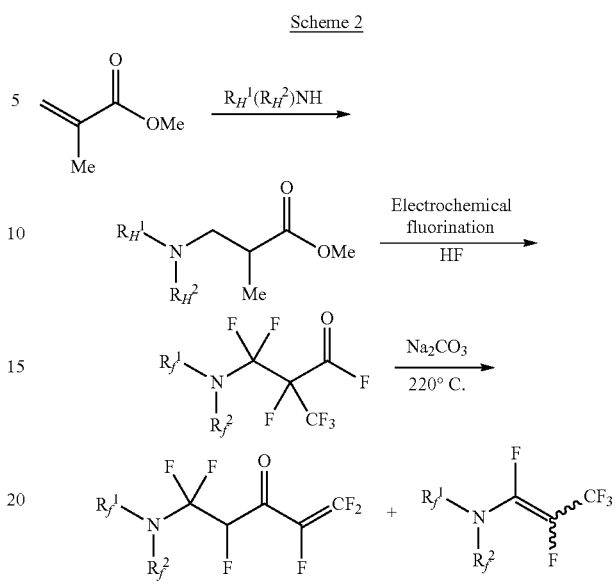

Scheme 2

In some embodiments, the present disclosure is further directed to working fluids that include the above-described propenylamine compounds as a major component. For example, the working fluids may include at least 25%, at least 50%, at least 70%, at least 80%, at least 90%, at least 95%, or at least 99% by weight of the above-described propenylamine compounds based on the total weight of the working fluid. In addition to the propenylamine compounds, the working fluids may include a total of up to 75%, up to 50%, up to 30%, up to 20%, up to 10%, or up to 5% by weight of one or more of the following components: alcohols, ethers, alkanes, alkenes, haloalkenes, perfluorocarbons, perfluorinated tertiary amines, perfluoroethers, cycloalkanes, esters, ketones, oxiranes, aromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof, based on the total weight of the working fluid. Such additional components can be chosen to modify or enhance the properties of a composition for a particular use.

In some embodiments, the present disclosure is further directed to an apparatus for heat transfer that includes a device and a mechanism for transferring heat to or from the device. The mechanism for transferring heat may include a heat transfer working fluid that includes a 1-propenylamine compound of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, heat exchangers, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility suggests that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner.

The provided apparatus may include a mechanism for transferring heat. The mechanism may include a heat transfer fluid. The heat transfer fluid may include one or more 1-propenylamine compounds of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

Heat can be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath.

In some embodiments, the present disclosure is directed to a fire extinguishing composition. The composition may include one or more propenylamine compounds of the present disclosure and one or more co-extinguishing agents.

In illustrative embodiments, the co-extinguishing agent may include hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, hydrobromocarbons, bromochlorofluorocarbons, iodofluorocarbons, fluorinated ketones, hydrofluorocarbons, hydrochlorofluorocarbons, perfluorocarbons, perfluoropolyethers, hydrofluoroethers, hydrofluoropolyethers, chlorofluorocarbons, bromofluorocarbons, bromochlorofluorocarbons, iodofluorocarbons, hydrobromofluorocarbons, fluorinated ketones, hydrobromocarbons, fluorinated olefins, hydrofluoroolefins, fluorinated sulfones, fluorinated vinylethers, unsaturated fluoro-ethers, bromofluoroolefins, chlorofluoroolefins, iodofluoroolefins, fluorinated vinyl amines, fluorinated aminopropenes and mixtures thereof.

Such co-extinguishing agents can be chosen to enhance the extinguishing capabilities or modify the physical properties (e.g., modify the rate of introduction by serving as a propellant) of an extinguishing composition for a particular type (or size or location) of fire and can preferably be utilized in ratios (of co-extinguishing agent to propenylamine compound) such that the resulting composition does not form flammable mixtures in air.

In some embodiments, the propenylamine compounds and the co-extinguishing agent may be present in the fire extinguishing composition in amounts sufficient to suppress or extinguish a fire. The propenylamine compounds and the co-extinguishing agent can be in a weight ratio of from about 9:1 to about 1:9.

In some embodiments, the present disclosure is directed to an apparatus for converting thermal energy into mechanical energy in a Rankine cycle. The apparatus may include a working fluid that includes one or more propenylamine compounds of the present disclosure. The apparatus may further include a heat source to vaporize the working fluid and form a vaporized working fluid, a turbine through which the vaporized working fluid is passed thereby converting thermal energy into mechanical energy, a condenser to cool the vaporized working fluid after it is passed through the turbine, and a pump to recirculate the working fluid.

In some embodiments, the present disclosure relates to a process for converting thermal energy into mechanical energy in a Rankine cycle. The process may include using a heat source to vaporize a working fluid that includes one or more propenylamine compounds of the present disclosure to form a vaporized working fluid. In some embodiments, the heat is transferred from the heat source to the working fluid in an evaporator or boiler. The vaporized working fluid may pressurized and can be used to do work by expansion. The heat source can be of any form such as from fossil fuels, e.g., oil, coal, or natural gas. Additionally, in some embodiments, the heat source can come from nuclear power, solar power, or fuel cells. In other embodiments, the heat can be "waste heat" from other heat transfer systems that would otherwise be lost to the atmosphere. The "waste heat," in some embodiments, can be heat that is recovered from a second Rankine cycle system from the condenser or other cooling device in the second Rankine cycle.

An additional source of "waste heat" can be found at landfills where methane gas is flared off. In order to prevent methane gas from entering the environment and thus contributing to global warming, the methane gas generated by the landfills can be burned by way of "flares" producing carbon dioxide and water which are both less harmful to the environment in terms of global warming potential than methane. Other sources of "waste heat" that can be useful in the provided processes are geothermal sources and heat from other types of engines such as gas turbine engines that give off significant heat in their exhaust gases and to cooling liquids such as water and lubricants.

In the provided process, the vaporized working fluid may expanded though a device that can convert the pressurized working fluid into mechanical energy. In some embodiments, the vaporized working fluid is expanded through a turbine which can cause a shaft to rotate from the pressure of the vaporized working fluid expanding. The turbine can then be used to do mechanical work such as, in some embodiments, operate a generator, thus generating electricity. In other embodiments, the turbine can be used to drive belts, wheels, gears, or other devices that can transfer mechanical work or energy for use in attached or linked devices.

After the vaporized working fluid has been converted to mechanical energy the vaporized (and now expanded) working fluid can be condensed using a cooling source to liquefy for reuse. The heat released by the condenser can be used for other purposes including being recycled into the same or another Rankine cycle system, thus saving energy. Finally, the condensed working fluid can be pumped by way of a pump back into the boiler or evaporator for reuse in a closed system.

The desired thermodynamic characteristics of organic Rankine cycle working fluids are well known to those of ordinary skill and are discussed, for example, in U.S. Pat. Appl. Publ. No. 2010/0139274 (Zyhowski et al.) The greater the difference between the temperature of the heat source and the temperature of the condensed liquid or a provided heat sink after condensation, the higher the Rankine cycle thermodynamic efficiency. The thermodynamic efficiency is influenced by matching the working fluid to the heat source temperature. The closer the evaporating temperature of the working fluid to the source temperature, the higher the efficiency of the system. Toluene can be used, for example, in the temperature range of 79° C. to about 260° C., however toluene has toxicological and flammability concerns. Fluids such as 1,1-dichloro-2,2,2-trifluoroethane and 1,1,1,3,3-pentafluoropropane can be used in this temperature range as an alternative. But 1,1-dichloro-2,2,2-trifluoroethane can form toxic compounds below 300° C. and need to be limited to an evaporating temperature of about 93° C. to about 121° C. Thus, there is a desire for other environmentally-friendly Rankine cycle working fluids with higher critical temperatures so that source temperatures such as gas turbine and internal combustion engine exhaust can be better matched to the working fluid.

In some embodiments, the present disclosure relates to the use of the propenylamine compounds of the present disclosure as nucleating agents in the production of polymeric foams and in particular in the production of polyurethane foams and phenolic foams. In this regard, in some embodiments, the present disclosure is directed to a foamable composition that includes one or more blowing agents, one or more foamable polymers or precursor compositions thereof, and one or more nucleating agents that include a 1-propenylamine compound of the present disclosure.

In some embodiments, a variety of blowing agents may be used in the provided foamable compositions including liquid or gaseous blowing agents that are vaporized in order to foam the polymer or gaseous blowing agents that are generated in situ in order to foam the polymer. Illustrative examples of blowing agents include hydrochlorofluorocarbons (HCFCs), hydrofluorocarbons (HFCs), hydrochlorocarbons (HCCs), iodofluorocarbons (IFCs), hydrocarbons, hydrofluoroolefins (HFOs) and hydrofluoroethers (HFEs). The blowing agent for use in the provided foamable compositions can have a boiling point of from about −45° C. to about 100° C. at atmospheric pressure. Typically, at atmospheric pressure the blowing agent has a boiling point of at least about 15° C., more typically between about 20° C. and about 80° C. The blowing agent can have a boiling point of between about 30° C. and about 65° C. Further illustrative examples of blowing agents that can be used include aliphatic and cycloaliphatic hydrocarbons having about 5 to about 7 carbon atoms, such as n-pentane and cyclopentane, esters such as methyl formate, HFCs such as $CF_3CF_2CHFCHFCF_3$, $CF_3CH_2CF_2H$, $CF_3CH_2CF_2CH_3$, $CF_3CF_2H$, $CH_3CF_2H$(HFC-152a), $CF_3CH_2CH_2CF_3$ and $CHF_2CF_2CH_2F$, HCFCs such as $CH_3CCl_2F$, $CF_3CHCl_2$, and $CF_2HCl$, HCCs such as 2-chloropropane, and IFCs such as $CF_3I$, and HFEs such as $C_4F_9OCH_3$ and HFOs such as $CF_3CF=CH_2$, $CF_3CH=CHF$, $CF_3CH=CHCl$, and $CF_3CH=CHCF_3$ In certain formulations $CO_2$ generated from the reaction of water with foam precursor such as an isocyanate can be used as a blowing agent.

In various embodiments, the provided foamable composition may also include one or more foamable polymers or a precursor composition thereof. Foamable polymers suitable for use in the provided foamable compositions include, for example, polyolefins, e.g., polystyrene, poly(vinyl chloride), and polyethylene. Foams can be prepared from styrene polymers using conventional extrusion methods. The blowing agent composition can be injected into a heat-plastified styrene polymer stream within an extruder and admixed therewith prior to extrusion to form foam. Representative examples of suitable styrene polymers include, for example, the solid homopolymers of styrene, α-methylstyrene, ring-alkylated styrenes, and ring-halogenated styrenes, as well as copolymers of these monomers with minor amounts of other readily copolymerizable olefinic monomers, e.g., methyl methacrylate, acrylonitrile, maleic anhydride, citraconic anhydride, itaconic anhydride, acrylic acid, N-vinylcarbazole, butadiene, and divinylbenzene. Suitable vinyl chloride polymers include, for example, vinyl chloride homopolymer and copolymers of vinyl chloride with other vinyl monomers. Ethylene homopolymers and copolymers of ethylene with, e.g., 2-butene, acrylic acid, propylene, or butadiene may also be useful. Mixtures of different types of polymers can be employed.

In various embodiments, the foamable compositions of the present disclosure may have a molar ratio of nucleating agent to blowing agent of no more than 1:50, 1:25, 1:9, or 1:7, 1:3, or 1:2.

Other conventional components of foam formulations can, optionally, be present in the foamable compositions of the present disclosure. For example, cross-linking or chain-extending agents, foam-stabilizing agents or surfactants, catalysts and fire-retardants can be utilized. Other possible components include fillers (e.g., carbon black), colorants, fungicides, bactericides, antioxidants, reinforcing agents, antistatic agents, and other additives or processing aids.

In some embodiments, polymeric foams can be prepared by vaporizing at least one liquid or gaseous blowing agent or generating at least one gaseous blowing agent in the presence of at least one foamable polymer or a precursor composition thereof and a nucleating agent as described above. In further embodiments, polymeric foams can be prepared using the provided foamable compositions by vaporizing (e.g., by utilizing the heat of precursor reaction) at least one blowing agent in the presence of a nucleating agent as described above, at least one organic polyisocyanate and at least one compound containing at least two reactive hydrogen atoms. In making a polyisocyanate-based foam, the polyisocyanate, reactive hydrogen-containing compound, and blowing agent composition can generally be combined, thoroughly mixed (using, e.g., any of the various known types of mixing head and spray apparatus), and permitted to expand and cure into a cellular polymer. It is often convenient, but not necessary, to preblend certain of the components of the foamable composition prior to reaction of the polyisocyanate and the reactive hydrogen-containing compound. For example, it is often useful to first blend the reactive hydrogen-containing compound, blowing agent composition, and any other components (e.g., surfactant) except the polyisocyanate, and to then combine the resulting mixture with the polyisocyanate. Alternatively, all components of the foamable composition can be introduced separately. It is also possible to pre-react all or a portion of the reactive hydrogen-containing compound with the polyisocyanate to form a prepolymer.

In some embodiments, the present disclosure is directed to dielectric fluids that include one or more propenylamine compounds of the present disclosure, as well as to electrical devices (e.g., capacitors, switchgear, transformers, or electric cables or buses) that include such dielectric fluids. For purposes of the present application, the term "dielectric fluid" is inclusive of both liquid dielectrics and gaseous dielectrics. The physical state of the fluid, gaseous or liquid, is determined at the operating conditions of temperature and pressure of the electrical device in which it is used.

In some embodiments, the dielectric fluids include one or more propenylamine compounds of the present disclosure and, optionally, one or more second dielectric fluids. Suitable second dielectric fluids include, for example, air, nitrogen, helium, argon, and carbon dioxide, or combinations thereof. The second dielectric fluid may be a non-condensable gas or an inert gas. Generally, the second dielectric fluid may be used in amounts such that vapor pressure is at least 70 kPa at 25° C., or at the operating temperature of the electrical device.

The dielectric fluids of the present application are useful for electrical insulation and for arc quenching and current interruption equipment used in the transmission and distribution of electrical energy. Generally, there are three major types of electrical devices in which the fluids of the present disclosure can be used: (1) gas-insulated circuit breakers and current-interruption equipment, (2) gas-insulated transmission lines, and (3) gas-insulated transformers. Such gas-insulated equipment is a major component of power transmission and distribution systems.

In some embodiments, the present disclosure provides electrical devices, such as capacitors, comprising metal electrodes spaced from each other such that the gaseous dielectric fills the space between the electrodes. The interior space of the electrical device may also comprise a reservoir of the liquid dielectric fluid which is in equilibrium with the gaseous dielectric fluid. Thus, the reservoir may replenish any losses of the dielectric fluid.

In some embodiments, the present disclosure relates to coating compositions that include a solvent composition that one or more propenylamine compounds of the present disclosure, and one or more coating materials which are soluble or dispersible in the solvent composition.

In various embodiments, the coating materials of the coating compositions may include pigments, lubricants, stabilizers, adhesives, anti-oxidants, dyes, polymers, pharmaceuticals, release agents, inorganic oxides, and the like, and combinations thereof. For example, coating materials may include perfluoropolyether, hydrocarbon, and silicone lubricants; amorphous copolymers of tetrafluoroethylene; polytetrafluoroethylene; or combinations thereof. Further examples of suitable coating materials include titanium dioxide, iron oxides, magnesium oxide, perfluoropolyethers, polysiloxanes, stearic acid, acrylic adhesives, polytetrafluoroethylene, amorphous copolymers of tetrafluoroethylene, or combinations thereof.

In some embodiments, the above-described coating compositions can be useful in coating deposition, where the propenylamine compounds function as a carrier for a coating material to enable deposition of the material on the surface of a substrate. In this regard, the present disclosure further relates to a process for depositing a coating on a substrate surface using the coating composition. The process comprises the step of applying to at least a portion of at least one surface of a substrate a coating of a liquid coating composition comprising (a) a solvent composition containing one or more of the 1-propenylamine compounds; and (b) one or more coating materials which are soluble or dispersible in the solvent composition. The solvent composition can further comprise one or more co-dispersants or co-solvents and/or one or more additives (e.g., surfactants, coloring agents, stabilizers, anti-oxidants, flame retardants, and the like). Preferably, the process further comprises the step of removing the solvent composition from the coating by, e.g., allowing evaporation (which can be aided by the application of, e.g., heat or vacuum).

In various embodiments, to form a coating composition, the components of the coating composition (i.e., the propenylamine compound(s), the coating material(s), and any co-dispersant(s) or co-solvent(s) utilized) can be combined by any conventional mixing technique used for dissolving, dispersing, or emulsifying coating materials, e.g., by mechanical agitation, ultrasonic agitation, manual agitation, and the like. The solvent composition and the coating material(s) can be combined in any ratio depending upon the desired thickness of the coating. For example, the coating material(s) may constitute from about 0.1 to about 10 weight percent of the coating composition.

In illustrative embodiments, the deposition process of the disclosure can be carried out by applying the coating composition to a substrate by any conventional technique. For example, the composition can be brushed or sprayed (e.g., as an aerosol) onto the substrate, or the substrate can be spin-coated. In some embodiments, the substrate may be coated by immersion in the composition. Immersion can be carried out at any suitable temperature and can be maintained for any convenient length of time. If the substrate is a tubing, such as a catheter, and it is desired to ensure that the composition coats the lumen wall, the composition may be drawn into the lumen by the application of reduced pressure.

In various embodiments, after a coating is applied to a substrate, the solvent composition can be removed from the coating (e.g., by evaporation). If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

Both organic and inorganic substrates can be coated by the processes of the present disclosure. Representative examples of the substrates include metals, ceramics, glass, polycarbonate, polystyrene, acrylonitrile-butadiene-styrene copolymer, natural fibers (and fabrics derived therefrom) such as cotton, silk, fur, suede, leather, linen, and wool, synthetic fibers (and fabrics) such as polyester, rayon, acrylics, nylon, or blends thereof, fabrics including a blend of natural and synthetic fibers, and composites of the foregoing materials. In some embodiments, substrates that may be coated include, for example, magnetic hard disks or electrical connectors with perfluoropolyether lubricants or medical devices with silicone lubricants.

In some embodiments, the present disclosure relates to cleaning compositions that include one or more propenylamine compounds of the present disclosure, and one or more co-solvents.

In some embodiments, the propenylamine compounds may be present in an amount greater than 50 weight percent, greater than 60 weight percent, greater than 70 weight percent, or greater than 80 weight percent based upon the total weight of the propenylamine compounds and the co-solvent(s).

In various embodiments, the cleaning composition may further comprise a surfactant. Suitable surfactants include those surfactants that are sufficiently soluble in the fluorinated olefin, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylatedalkyl phenols, ethoxylated fatty acids, alkylarysulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble oil removal. The surfactant, if used, can be added in an amount sufficient to promote soil removal. Typically, surfactant is added in amounts from about 0.1 to 5.0 wt. %, preferably in amounts from about 0.2 to 2.0 wt. % of the cleaning composition.

In illustrative embodiments, the co-solvent may include alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof. Representative examples of co-solvents which can be used in the cleaning composition include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene, cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, or mixtures thereof.

In some embodiments, the present disclosure relates to a process for cleaning a substrate. The cleaning process can be carried out by contacting a contaminated substrate with a cleaning composition as discussed above. The propenylamine compounds can be utilized alone or in admixture with each other or with other commonly-used cleaning solvents, e.g., alcohols, ethers, alkanes, alkenes, haloalkenes, perfluorocarbons, perfluorinated tertiary amines, perfluoroethers, cycloalkanes, esters, ketones, oxiranes, aromatics, haloaromatics, siloxanes, hydrochlorocarbons, hydrochlorofluorocarbons, hydrofluorocarbons, hydrofluoroolefins, hydrochloroolefins, hydrochlorofluoroolefins, hydrofluoroethers, or mixtures thereof. Such co-solvents can be chosen to modify or enhance the solvency properties of a cleaning composition for a particular use and can be utilized in ratios (of co-solvent to 1-propenylamine compounds) such that the resulting composition has no flash point. If desirable for a particular application, the cleaning composition can further contain one or more dissolved or dispersed gaseous, liquid, or solid additives (for example, carbon dioxide gas, surfactants, stabilizers, antioxidants, or activated carbon).

In some embodiments, the present disclosure relates to cleaning compositions that include one or more propenylamine compounds of the present disclosure and optionally one or more surfactants. Suitable surfactants include those surfactants that are sufficiently soluble in the propenylamine compounds, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylated alkylphenols, ethoxylated fatty acids, alkylaryl sulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble soil removal. The surfactant, if used, can be added in an amount sufficient to promote soil removal. Typically, surfactant may be added in amounts from 0.1 to 5.0 wt. % or from 0.2 to 2.0 wt. % of the cleaning composition.

The cleaning processes of the disclosure can also be used to dissolve or remove most contaminants from the surface of a substrate. For example, materials such as light hydrocarbon contaminants; higher molecular weight hydrocarbon contaminants such as mineral oils and greases; fluorocarbon contaminants such as perfluoropolyethers, bromotrifluoroethylene oligomers (gyroscope fluids), and chlorotrifluoroethylene oligomers (hydraulic fluids, lubricants); silicone oils and greases; solder fluxes; particulates; water; and other contaminants encountered in precision, electronic, metal, and medical device cleaning can be removed.

The cleaning compositions can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies*, Electrochemical Publications Limited, Ayr, Scotland, pages 182-94 (1986).

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices.

In some embodiments, the present disclosure further relates to electrolyte compositions that include one or more propenylamine compounds of the present disclosure. The electrolyte compositions may comprise (a) a solvent composition including one or more of the 1-propenylamine compounds; and (b) at least one electrolyte salt. The electrolyte compositions of the present disclosure exhibit excellent oxidative stability, and when used in high voltage electrochemical cells (such as rechargeable lithium ion batteries) provide outstanding cycle life and calendar life. For example, when such electrolyte compositions are used in an electrochemical cell with a graphitized carbon electrode, the electrolytes provide stable cycling to a maximum charge voltage of at least 4.5V and up to 6.0V vs. Li/Li$^+$.

Electrolyte salts that are suitable for use in preparing the electrolyte compositions of the present disclosure include those salts that comprise at least one cation and at least one weakly coordinating anion (the conjugate acid of the anion having an acidity greater than or equal to that of a hydrocarbon sulfonic acid (for example, a bis(perfluoroalkanesulfonyl)imide anion); that are at least partially soluble in a selected propenylamine compound (or in a blend thereof with one or more other propenylamine compounds or one or more conventional electrolyte solvents); and that at least partially dissociate to form a conductive electrolyte composition. The salts may be stable over a range of operating voltages, are non-corrosive, and are thermally and hydrolytically stable. Suitable cations include alkali metal, alkaline earth metal, Group IIB metal, Group IIIB metal, transition metal, rare earth metal, and ammonium (for example, tetraalkylammonium or trialkylammonium) cations, as well as a proton. In some embodiments, cations for battery use include alkali metal and alkaline earth metal cations. Suitable anions include fluorine-containing inorganic anions such as $(FSO_2)_2N^-$, $BF_4^-$, $PF_6^-$, $AsF_6^-$, and $SbF_6^-$; $ClO_4^-$; $HSO_4^-$; $H_2PO_4^-$; organic anions such as alkane, aryl, and alkaryl sulfonates; fluorine-containing and nonfluorinated tetraarylborates; carboranes and halogen-, alkyl-, or haloalkylsubstituted carborane anions including metallocarborane anions; and fluorine-containing organic anions such as perfluoroalkanesulfonates, cyanoperfluoroalkanesulfonylamides, bis(cyano)perfluoroalkanesulfonylmethides, bis(perfluoroalkanesulfonyl)imides, bis(perfluoroalkanesulfonyl)methides, and tris(perfluoroalkanesulfonyl)methides; and the like. Preferred anions for battery use include fluorine-containing inorganic anions (for example, $(FSO_2)_2N^-$, $BF_4^-$, $PF_6^-$, and $AsF_6^-$) and fluorine-containing organic anions (for example, perfluoroalkanesulfonates, bis(perfluoroalkanesulfonyl)imides, and tris(perfluoroalkanesulfonyl)methides). The fluorine-containing organic anions can be either fully fluorinated, that is perfluorinated, or partially fluorinated (within the organic portion thereof). In some embodiments, the fluorine-containing organic anion is at least about 80 percent fluorinated (that is, at least about 80 percent of the carbon-bonded substituents of the anion are fluorine atoms). In some embodiments, the anion is perfluorinated (that is, fully fluorinated, where all of the carbon-bonded substituents are fluorine atoms). The anions, including the perfluorinated anions, can contain one or more catenary heteroatoms such as, for example, nitrogen, oxygen, or sulfur. In some embodiments, fluorine-containing organic anions include perfluoroalkanesulfonates, bis(perfluoroalkanesulfonyl)imides, and tris(perfluoroalkanesulfonyl)methides.

In some embodiments, the electrolyte salts may include lithium salts. Suitable lithium salts include, for example, lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis (fluorosulfonyl)imide (Li—FSI), and mixtures of two or more thereof.

The electrolyte compositions of the present disclosure can be prepared by combining at least one electrolyte salt and a solvent composition including at least one propenylamine compound of the present disclosure, such that the salt is at least partially dissolved in the solvent composition at the desired operating temperature. The propenylamine compounds (or a normally liquid composition including, consisting, or consisting essentially thereof) can be used in such preparation.

In some embodiments, the electrolyte salt is employed in the electrolyte composition at a concentration such that the conductivity of the electrolyte composition is at or near its maximum value (typically, for example, at a Li molar concentration of around 0.1-4.0 M, or 1.0-2.0 M, for electrolytes for lithium batteries), although a wide range of other concentrations may also be employed.

In some embodiments, one or more conventional electrolyte solvents are mixed with the propenylamine compound(s) (for example, such that the propenylamine(s) constitute from about 1 to about 80 or 90 percent of the resulting solvent composition). Useful conventional electrolyte solvents include, for example, organic and fluorine-containing electrolyte solvents (for example, propylene carbonate, ethylene carbonate, dimethyl carbonate, diethyl carbonate, ethyl methyl carbonate, dimethoxyethane, 7-butyrolactone, diglyme (that is, diethylene glycol dimethyl ether), tetraglyme (that is, tetraethylene glycol dimethyl ether), monofluoroethylene carbonate, vinylene carbonate, ethyl acetate, methyl butyrate, tetrahydrofuran, alkyl-substituted tetrahydrofuran, 1,3-dioxolane, alkyl-substituted 1,3-dioxolane, tetrahydropyran, alkyl-substituted tetrahydropyran, and the like, and mixtures thereof). Other conventional electrolyte additives (for example, a surfactant) can also be present, if desired.

The present disclosure further relates to electrochemical cells (e.g., fuel cells, batteries, capacitors, electrochromic windows) that include the above-described electrolyte compositions. Such an electrochemical cell may include a positive electrode, a negative electrode, a separator, and the above-described electrolyte composition.

A variety of negative and positive electrodes may be employed in the electrochemical cells. Representative negative electrodes include graphitic carbons e.g., those having a spacing between (002) crystallographic planes, $d_{002}$, of 3.45 Å>$d_{002}$>3.354 Å and existing in forms such as powders, flakes, fibers or spheres (e.g., mesocarbon microbeads); $Li_{4/3}Ti_{5/3}O_4$ the lithium alloy compositions described in U.S. Pat. No. 6,203,944 (Turner '944) entitled "ELECTRODE FOR A LITHIUM BATTERY" and PCT Published Patent Application No. WO 00103444 (Turner PCT) entitled "ELECTRODE MATERIAL AND COMPOSITIONS"; and combinations thereof. Representative positive electrodes include $LiFePO_4$, $LiMnPO_4$, $LiCoPO_4$, $LiMn_2O_4$, $LiCoO_2$ and combinations thereof. The negative or positive electrode may contain additives such as will be familiar to those skilled in the art, e. g., carbon black for negative electrodes and carbon black, flake graphite and the like for positive electrodes.

The electrochemical devices of the present disclosure can be used in various electronic articles such as computers, power tools, automobiles, telecommunication devices, and the like.

Embodiments

1. A composition comprising a perfluorinated propenylamine represented by the following general formula (1):

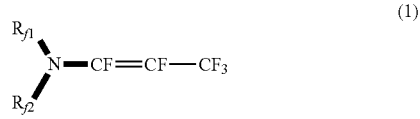

wherein each occurrence of $R_{f1}$ and $R_{f2}$ is:
   (i) independently a linear or branched perfluoroalkyl group having 1-8 carbon atoms and optionally comprises one or more catenated heteroatoms; or
   (ii) bonded together to form a ring structure having 4-8 carbon atoms and that optionally comprises one or more catenated heteroatoms; and
   wherein at least 60 wt. % of the perfluorinated propenylamine is in the form of the E isomer, based on the total weight of the perfluorinated propenylamine in the composition.

2. The composition of embodiment 1, wherein at least 70 wt. % of the perfluorinated propenylamine is in the form of the E isomer, based on the total weight of the perfluorinated propenylamine in the composition.

3. The composition of any one of embodiments 1-2, wherein each occurrence of $R_{f1}$ and $R_{f2}$ is independently a linear or branched perfluoroalkyl group having 1-8 carbon atoms and optionally comprises one or more catenated heteroatoms.

4. The composition of any one of embodiments 1-2, wherein each occurrence of $R_{f1}$ and $R_{f2}$ is bonded together to form a ring structure having 4-8 carbon atoms and that optionally comprises one or more catenated heteroatoms.

5. The composition of any one of embodiments 1-4, wherein the perfluorinated propenylamine has a GWP of less than 100.

6. A method of making the composition of any one of embodiments 1-5, the method comprising:
   contacting a perfluorinated allylamine of general formula (2) with an active isomerization catalyst;

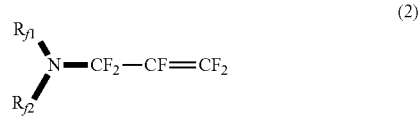

carrying out a selective catalytic isomerization to form a 1-propenylamine of general formula (1);

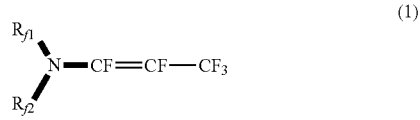

wherein the selectivity for formation of the E isomer of formula (1) is at least 70% wt. %, based on the total weight of the propenylamine in the composition.

7. A working fluid comprising a composition according to any one of embodiments 1-5, wherein the composition is present in the working fluid at an amount of at least 25% by weight based on the total weight of the working fluid.

8. An apparatus for heat transfer comprising:
   a device; and
   a mechanism for transferring heat to or from the device, the mechanism comprising a heat transfer fluid that comprises the composition or working fluid according to any one of embodiments 1-5 or 7.

9. An apparatus for heat transfer according to embodiment 8, wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

10. An apparatus for heat transfer according to embodiment 8, wherein the mechanism for transferring heat is a component in a system for maintaining a temperature or temperature range of an electronic device.

11. A method of transferring heat comprising:
    providing a device; and
    transferring heat to or from the device using a heat transfer fluid that the composition or working fluid according to any one of embodiments 1-5 or 7.

12. The composition or working fluid of any one of embodiments 1-5 or 7, wherein at least 95 wt. % of the perfluorinated propenylamine is in the form of the E isomer, based on the total weight of the perfluorinated propenylamine in the composition.

The operation of the present disclosure will be further described with regard to the following detailed examples. These examples are offered to further illustrate various embodiments and techniques. It should be understood, however, that many variations and modifications may be made while remaining within the scope of the present disclosure.

EXAMPLES

Objects and advantages of this disclosure are further illustrated by the following comparative and illustrative examples.

| List of Materials: | | |
|---|---|---|
| Name | Description | Source |
| Antimony(V) Fluoride | $SbF_5$ | Acros Organics, New Jersey |
| Niobium(V) Fluoride | $NbF_5$ | Oakwood Chemical, W. Columbia, SC |
| Titanium(IV) Fluoride | $TiF_4$ | Alfa-Aesar, Ward Hill, MA |
| Zirconium(IV) Fluoride | $ZrF_4$ | Alfa-Aesar, Ward Hill, MA |
| Tantalum(V) Fluoride | $TaF_5$ | Oakwood Chemical, W. Columbia, SC |
| Fluoroantimonic acid | $HSbF_6$ | Aldrich, Milwaukee, WI |
| Antimony (V) dichlorotrifluoride | $SbCl_2F_3$ | Oakwood Chemical, W. Columbia, SC |
| Antimony (V) tetrachloromonofluoride | $SbCl_4F$ | Oakwood Chemical, W. Columbia, SC |
| Triflic Acid (Anhydrous) | $CF_3SO_3H$ (> 99%) | Aldrich, Milwaukee, WI |
| Hydrogen Fluoride Pyridine | Pyridine-HF (70% HF) | Aldrich, Milwaukee, WI |

-continued

List of Materials:

| Name | Description | Source |
|---|---|---|
| Potassium bifluoride | KF-HF (99%) | Aldrich, Milwaukee, WI |
| Hydrofluoric acid (Anhydrous) | HF(g) | Matheson, New Brighton, MN |
| Cesium Fluoride (Anhydrous) | CsF Powder | Cabot Corp., Boston, MA |
| Potassium carbonate | $K_2CO_3$ | Aldrich, Milwaukee, WI |

Comparative Example 1

Propenylamine Isomer Distribution Prepared by Decarboxylation of Perfluorinated Acid Fluorides Over Potassium Carbonate The perfluorinated acid fluorides listed in Table 1 were prepared by electrochemical fluorination of the corresponding hydrocarbon esters, which were in turn prepared by Michael addition of the appropriate secondary hydrocarbon amines to methyl methacrylate using previously described methods that are well known in the art. Thermal decarboxylation of these perfluorinated acid fluorides over excess potassium carbonate according to methods described in WO 2015/095285 resulted in formation of a mixture of perfluorinated propenylamine isomers. Reaction conditions, total yield of propenylamine (sum of all 3 isomers) and the isomer distribution as determined by GC-FID are summarized in Table 1. GC peak assignments were confirmed by GC-MS and NMR spectroscopy. The percent of each isomer present, as determined by GC-FID area percent, is listed in Table 1, below. The results show that the Z-isomer of the internal olefin is consistently the major isomer formed, consistent with our finding that this is the thermodynamically most stable isomer.

Comparative Example 2

Catalyst Screening for E/Z Isomerization of 2,2,3,3,5,5,6,6-octafluoro-4-(1,2,3,3,3-pentafluoroprop-1-enyl)morpholine and Determination of the Equilibrium E:Z Isomer Ratio

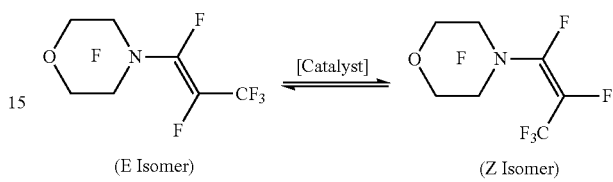

(E Isomer)     (Z Isomer)

2,2,3,3,5,5,6,6-octafluoro-4-(1,2,3,3,3-pentafluoroprop-1-enyl)morpholine was prepared as a 44:56 ratio of E and Z isomers and an overall purity of 98.5% by GC using the procedure described in Example 2 of WO 2015/095285. Non-equilibrium mixtures of E and Z isomers were then generated by fractional distillation and isolation of the early and late distillation cuts. These high purity mixtures were then used in catalyst screening experiments to determine which catalysts were active for E/Z isomerization at temperatures ranging from 20-88° C. The catalyzed isomerization reactions were run neat (in the absence of solvent) under a dry nitrogen atmosphere to prevent catalyst poisoning by water. The catalysts and conditions used in each experiment and the starting and final E:Z ratios are summarized in Table 2, below.

TABLE 1

Reaction Conditions and Isomer Distribution of Comparative Example 1

| | | | Product Isomer Distribution | | |
|---|---|---|---|---|---|
| Input Acid Fluoride | Rxn Temp (° C.) | Total Olefin Yield (%) | (1A) E-Isomer | (1B) Z-Isomer | (2) Terminal Allyl Isomer |
| [morpholine structure] | 220 | 50 | 40.5 | 54.2 | 5.2 |
| [bis-CF3 amine structure] | 220 | 62 | 38.5 | 58.2 | 3.3 |

TABLE 2

Reaction Conditions and E:Z Ratios-Comparative Example 2

| Catalyst | Catalyst Loading (Wt %) | Reaction Time (Hrs) | Reaction Temp (° C.) | Starting E:Z Ratio | Final E:Z Ratio | Active? (Y/N) |
|---|---|---|---|---|---|---|
| SbF$_5$ | 2.82 | 67.0 | 20 | 20:80 | 22:78 | Y |
| SbF$_5$ | 8.27 | 67.5 | 20 | 62:38 | 33:67 | Y |
| SbF$_5$ | 5.55 | 24.0 | 88 | 20:80 | 32:68 | Y |
| HSbF$_6$ | 11.49 | 67.5 | 20 | 20:80 | 25:75 | Y |
| HSbF$_6$ | 10.36 | 67.5 | 20 | 62:38 | 32:68 | Y |
| NbF$_5$ | 7.37 | 97.0 | 20 | 62:38 | 62:38 | N |
| TaF$_5$ | 9.30 | 97.0 | 20 | 62:38 | 62:38 | N |
| SbCl$_4$F | 7.31 | 97.0 | 20 | 62:38 | 62:38 | N |
| SbCl$_2$F$_3$ | 8.83 | 97.0 | 20 | 62:38 | 62:38 | N |
| TiF$_4$ | 7.67 | 97.0 | 20 | 62:38 | 62:38 | N |
| ZrF$_4$ | 7.02 | 97.0 | 20 | 62:38 | 62:38 | N |
| CsF (Anhydrous Powder) | 6.56 | 21.5 | 20 | 20:80 | 20:80 | N |
| CF$_3$SO$_3$H (Anhydrous) | 22.2 | 67.5 | 20 | 62:38 | 62:38 | N |
| HF (Anhydrous) | 4.85 | 67.0 | 20 | 20:80 | 20:80 | N |
| KF-HF | 4.69 | 67.0 | 20 | 20:80 | 20:80 | N |
| HF-Pyridine (70% HF) | 12.42 | 67.0 | 20 | 20:80 | 20:80 | N |

Of the catalysts screened under these conditions, only SbF$_5$ and HSbF$_6$ showed appreciable catalyst activity for E/Z isomerization. As expected, catalyst activity and rate of isomerization was greater at higher temperatures. Interestingly, in the case of the SbF$_5$ or HSbF$_6$ catalysts, starting with either E-enriched or Z-enriched starting material resulted in approximately the same final E:Z ratio of 32:68, indicating that this must be the thermodynamic equilibrium ratio of isomers for 2,2,3,3,5,5,6,6-octafluoro-4-(1,2,3,3,3-pentafluoroprop-1-enyl)morpholine. Furthermore, it was noted that the E-enriched starting mixture reached equilibrium more quickly than the Z enriched starting mixture under similar reaction conditions, supporting the conclusion that the Z-isomer is the lower energy and thermodynamically preferred isomer. Thus, the Z isomer must overcome a larger activation barrier during isomerization to the E isomer versus the reverse reaction where E isomerizes to Z.

Comparative Example 3

Determination of Thermodynamically Favored Isomer for Various Perfluorinated 1-Propenylamines

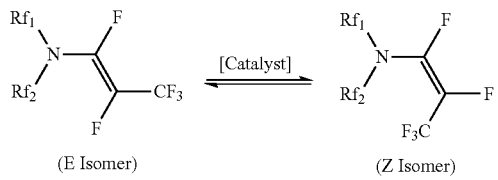

(E Isomer)   (Z Isomer)

Non-equilibrium, E-enriched mixtures of high purity perfluorinated 1-propenylamines, prepared by selective catalytic isomerization of the corresponding perfluorinated allyamines according to Example 2, were charged under a N$_2$ atmosphere into a dry 25 mL, 2-necked round-bottomed flask equipped with a water-cooled condenser and N$_2$ inlet. In the case of low boiling perfluorinated 1-propenylamines, such as 1,2,3,3,3-pentafluoro-N,N-bis(trifluoromethyl)prop-1-en-1-amine, a glass Fischer-Porter bottle equipped with a stainless steel pressure head was employed as the reactor to allow heating above boiling point without evaporative losses. In each case a catalytic amount of SbF$_5$ was added via plastic pipette to the neat propenylamine mixture and the flask (or pressure vessel) was immediately sealed and the reaction mixture heated to reaction temperature with stirring under N$_2$ and held at this temperature for the period of time indicated in Table 3. At the end of the reaction, the reaction mixture was chilled to less than −10° C. and quenched by gradual addition of methanol followed by excess water. After agitating vigorously, the quenched reaction mixture was allowed to phase separate and the lower fluorochemical phase was isolated and filtered through a 0.2 micron Teflon membrane via syringe to remove insoluble particulates. The clear filtrate was then analyzed neat by GC-FID. The final E:Z isomer ratios in the isolated product, as determined by GC, are summarized in Table 3, and the starting E:Z isomer ratios are provided for comparison. The GC assignments of E and Z isomers were confirmed by GC-MS and $^{19}$F NMR Spectroscopy. No significant side products were detected by GC, indicating that these catalyzed isomerization reactions are very clean. The results show that all of these isomerization reactions proceed toward an equilibrium ratio of isomers that favors the Z over the E isomer. Thus, this data indicates that for each of the Examples in Table 3, the Z isomer of the 1-propenylamine is the thermodynamically more stable isomer and the E isomer is thermodynamically less stable. Furthermore, this data suggests that the thermodynamic preference for the Z isomer is a general phenomenon for 1-propenylamines of general formula (1).

TABLE 3

Reaction Conditions and E:Z Ratios - Comparative Example 3

| 1-Propenylamine | Catalyst | Catalyst Loading (wt %) | Reaction Time (hr) | Reaction Temp (° C.) | Starting E:Z Ratio | Final E:Z Ratio |
|---|---|---|---|---|---|---|
| CF$_3$\N—CF=CFCF$_3$ / CF$_3$ | SbF$_5$ | 18.51 | 15 | 70 | 91.3:8.7 | 31.1:68.9 |

TABLE 3-continued

Reaction Conditions and E:Z Ratios - Comparative Example 3

| 1-Propenylamine | Catalyst | Catalyst Loading (wt %) | Reaction Time (hr) | Reaction Temp (° C.) | Starting E:Z Ratio | Final E:Z Ratio |
|---|---|---|---|---|---|---|
|  | SbF$_5$ | 12.5 | 20 | 80 | 99.7:0.3 | 33.3:66.7 |

Example 1

Selective Isomerization of 2,2,3,3,5,5,6,6-octafluoro-4-(perfluoroallyl)morpholine to E-2,2,3,3,5,5,6,6-octafluoro-4-(1,2,3,3,3-pentafluoroprop-1-enyl)morpholine Using Various Transition Metal Fluoride Catalysts

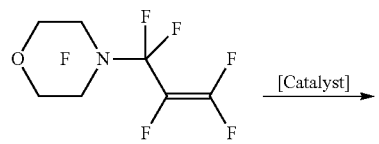

(Terminal Allyl Isomer)

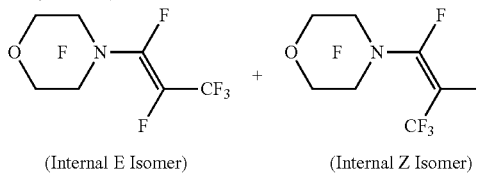

(Internal E Isomer)   (Internal Z Isomer)

Samples of 2,2,3,3,5,5,6,6-octafluoro-4-(perfluoroallyl)morpholine of greater than 98% purity (prepared using the procedure described in Example 2 of WO 2015/095285) were charged to a dry Pyrex round-bottomed flask equipped with a water cooled condenser and nitrogen inlet. The perfluorinated allyl-morpholine starting material was then combined with catalytic amounts of various anhydrous transition metal fluorides under a nitrogen atmosphere and allowed to react with magnetic stirring in the absence of solvent at the temperature and for the period of time indicated in Table 4. At the end of the reaction, the reaction mixture was filtered at ambient temperature through a 0.45 micron Teflon membrane via syringe to remove insoluble catalyst and the clear filtrate was then analyzed neat by GC-FID. The percent conversion of the terminal allyl starting material to internal olefin isomers (E&Z combined) and the E:Z isomer ratio in the final isolated product, as determined by GC, is summarized in Table 4. The GC assignments of E and Z isomers were confirmed by GC-MS and $^{19}$F NMR Spectroscopy. No significant side products were detected by GC, indicating that these catalyzed isomerization reactions are very clean. The results surprisingly indicate that these isomerization catalysts are highly selective in isomerizing the perfluorinated allylmorpholine to the thermodynamically disfavored E-isomer of the internal olefin. In each case, very little of the thermodynamically favored Z isomer is formed, even at relatively high temperatures, up to 85° C. Thus, this catalyzed isomerization reaction represents a selective and cost effective method of producing highly E-enriched 2,2,3,3,5,5,6,6-octafluoro-4-(1,2,3,3,3-pentafluoroprop-1-enyl)morpholine in high yield and in high overall purity.

TABLE 4

Reaction Conditions and E:Z Ratios—Example 1

| Catalyst | Catalyst Loading (Wt %) | Reaction Time (Hrs) | Reaction Temp. (° C.) | % Conversion (by GC-FID) | Final E:Z Isomer Ratio |
|---|---|---|---|---|---|
| TaF$_5$ | 12.61 | 88.5 | 20 | 99.60 | 98.1:1.9 |
| ZrF$_4$ | 8.06 | 18.5 | 85 | 84.09 | 96.6:3.4 |
| TiF$_4$ | 9.77 | 18.5 | 85 | 99.89 | 92.9:7.1 |
| NbF$_5$ | 1.19 | 3.0 | 85 | 99.99 | 98.3:1.7 |

Example 2

Selective Isomerization of Various Other Perfluorinated Allylamines to E-1-propenylamines Using NbF$_5$ Catalyst

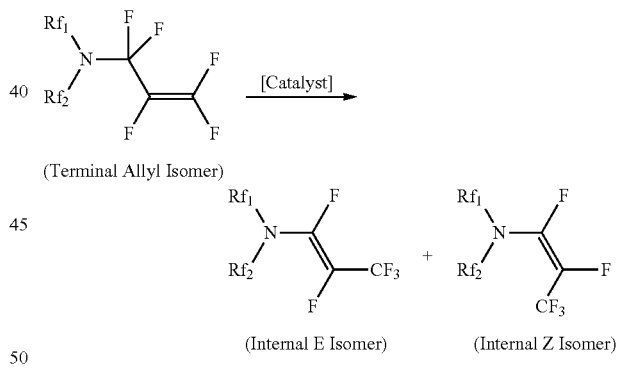

High purity samples of the perfluorinated allylamines in Table 5 were independently charged to a dry Pyrex round-bottomed flask equipped with a water cooled condenser and nitrogen inlet. In the case of low boiling perfluorinated allylamines, such as 1,1,2,3,3-pentafluoro-N,N-bis(trifluoromethyl)prop-2-en-1-amine, a glass Fischer-Porter bottle equipped with a stainless steel pressure head was employed as the reactor to allow heating above boiling point without evaporative losses. The perfluorinated allylamine starting material was then combined with a catalytic amount of anhydrous NbF$_5$ under a nitrogen atmosphere and allowed to react with stirring in the absence of solvent at the temperature and for the period of time indicated in Table 5. At the end of the reaction, the reaction mixture was filtered at room temperature through a 0.45 micron Teflon membrane via syringe to remove insoluble catalyst and the clear filtrate was then analyzed neat by GC-FID. The percent conversion of the terminal allyl starting material to internal olefin isomers (E&Z combined) and the final E:Z isomer ratio in the isolated product, as determined by GC, is summarized in Table 5. The GC assignments of E and Z isomers was confirmed by GC-MS and $^{19}$F NMR Spectroscopy. No significant side products were detected by GC, indicating that these catalyzed isomerization reactions are very clean. The results indicate that all of these isomerization reactions are highly selective in forming the thermodynamically disfavored E-isomer of the internal olefin. In each case, very little of the thermodynamically favored Z isomer is formed. Thus, these catalyzed isomerization reactions represent a general method of selectively producing highly E-enriched 1-propenylamines in high yield and in high overall purity.

In a 2-neck round bottomed flask equipped with magnetic stir bar, rubber septum, and inlet adapter connected to a dry nitrogen source, neat 2,2,3,3,5,5,6,6-octafluoro-4-(1,1,2,3,3-pentafluoroallyl)morpholine (20 g, 55.3 mmol) was slowly treated at 0° C., with SbF$_5$ (0.6 g, 3 mmol). The resulting solution was allowed to stir at 0° C. for 1 h, and the reaction was then quenched by addition of water (10 mL) at 0° C. The lower fluorochemical product phase was separated and dried over Na$_2$SO$_4$. Filtration to remove the desiccating agent yielded 18 g of clear liquid product. Analysis by GC-FID revealed 85+% conversion of terminal allylic double bond to internal double bond and a final E:Z ratio of 97:3 for the 1-propenylamine product produced. The GC assignments of E and Z isomers were confirmed by GC-MS and $^{19}$F NMR spectroscopy.

TABLE 5

Reaction Conditions and E:Z Ratios - Example 2

| Perfluorinated Allylamine | NbF$_5$ Catalyst Loading (Wt %) | Reaction Time (Hrs) | Reaction Temp. (° C.) | % Conversion (by GC-FID) | Final E:Z Isomer Ratio |
|---|---|---|---|---|---|
| 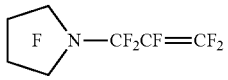 | 4.14 | 3 | 80 | 99.6 | 99.7:0.3 |
| 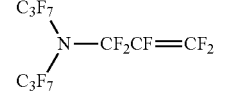 | 5.58 | 3 | 90 | 99.4 | 97.3:2.7 |
| 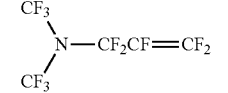 | 3.80 | 3 | 75 | 99.67 | 91.3:8.7 |

Example 3

Selective Isomerization of 2,2,3,3,5,5,6,6-octafluoro-4-(1,1,2,3,3-pentafluoroprop-2-enyl)morpholine to 2,2,3,3,5,5,6,6-octafluoro-4-[(E)-1,2,3,3,3-pentafluoroprop-1-enyl]morpholine Using SbF$_5$ Catalyst

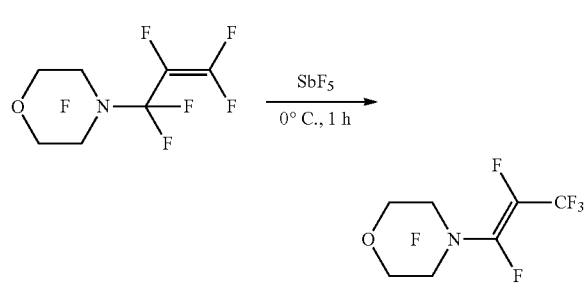

Example 4

Selective Isomerization of 1,1,2,3,3-pentafluoro-N,N-bis(trifluoromethyl)-prop-2-en-1-amine to (E)-1,1,2,3,3-pentafluoro-N,N-bis(trifluoromethyl)-prop-1-en-1-amine Using SbF$_5$ Catalyst

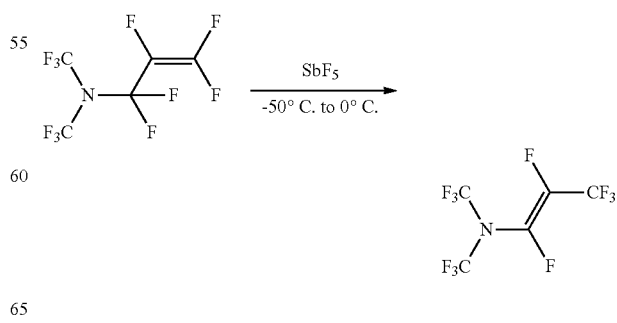

In a 2-neck round bottomed flask equipped with magnetic stir bar, rubber septum, and inlet adapter connected to a dry nitrogen source, neat 1,1,2,3,3-pentafluoro-N,N-bis(trifluoromethyl)-prop-2-en-1-amine (25 g, 88.3 mmol) was slowly treated at −50° C., with SbF$_5$ (1.0 g, 4.6 mmol). The resulting solution was allowed to slowly warm to 0° C. over 60 min, and was stirred at this temperature for 30 min. The reaction was subsequently quenched by addition of water (10 mL) at 0° C. The lower fluorochemical phase was separated and dried over Na$_2$SO$_4$. Filtration to remove the desiccating agent yielded 20 g of clear liquid product. Analysis of the product by GC-FID revealed 98+% conversion of the terminal allylic double bond to internal double bond and a final E:Z ratio of 93:7 for the 1-propenylamine product produced. The GC assignments of E and Z isomers were confirmed by GC-MS and $^{19}$F NMR spectroscopy.

Example 5

Atmospheric Lifetimes and Estimated GWPs of E and Z-1-Propenylamines

The atmospheric lifetimes of 1-propenylamines were determined from their rate of reaction with hydroxyl radicals. The pseudo-first order rates for the reaction of the gaseous 1-propenylamines with hydroxyl radical were measured in a series of experiments relative to reference compounds such as chloromethane and ethane. The measurements were performed in a 5.7 L, heated FTIR gas cell equipped with a polished semiconductor-grade quartz window. An Oriel Instruments UV Lamp, Model 66921 equipped with a 480 W mercury-xenon bulb was used to generate hydroxyl radicals by photolyzing ozone in the presence of water vapor. The concentrations of the 1-propenylamine and the reference compound were measured as a function of reaction time using an I-Series FTIR from Midac Corporation. The atmospheric lifetimes were calculated from the reaction rates for the 1-propenylamines relative to the reference compounds and the reported lifetime of the reference compounds as shown below:

$$\tau_x = \tau_r \cdot \frac{k_r}{k_x}$$

where $\tau_x$ is the atmospheric lifetime of the 1-propenylamine, $\tau_r$ is the atmospheric lifetime of the reference compound, and $k_x$ and $k_r$ are the rate constants for the reaction of hydroxyl radical with the isomeric 1-propenylamines and the reference compound, respectively.

Global warming potentials (GWPs) have been estimated for the 1-propenylamine isomers using these atmospheric lifetimes. The GWPs were calculated according to the Intergovernmental Panel on Climate Change (IPCC) 2013 method using a 100 year integration time horizon (ITH). The radiative efficiencies used in these calculations were based upon the infrared cross-sections measured on the mixture of E and Z isomers for each 1-propenylamine. Results for the E and Z isomers of 1-propenylamines are shown in Table 6.

TABLE 6

Measured Atmospheric Lifetimes and Estimated GWPs of E and Z-1-Propenylamines

| 1-Propenylamine | Atmospheric Lifetime (Yrs) | | Estimated GWP (100-yr ITH) | |
|---|---|---|---|---|
| | E-isomer | Z-isomer | E-isomer | Z-isomer |
| (CF$_3$)$_2$N—CF=CFCF$_3$ | 0.71 | 1.9 | 50 | 140 |
| C$_2$F$_5$(CF$_3$)N—CF=CFCF$_3$ | 1.4 | 3.5 | 110 | 270 |
| ![morpholine]O(C$_4$H$_7$F)N—CF=CFCF$_3$ | 0.80 | 2.6 | 80 | 250 |

Example 6

Isomerization of 2,2,3,3,5,5,6,6-octafluoro-4-(1,1,2,3,3-pentafluoroprop-2-enyl)morpholine to (E)-2,2,3,3,5,5,6,6-octafluoro-4-(1,2,3,3,3-pentafluoroprop-1-enyl)morpholine with AlCl$_3$

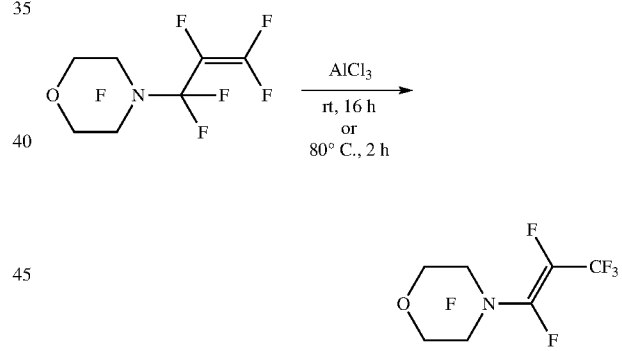

In a 25-mL two-neck round bottom flask equipped with magnetic stir bar, thermocouple, and inlet adapter connected via tubing to a Schlenk line, 2,2,3,3,5,5,6,6-octafluoro-4-(1,1,2,3,3-pentafluoroprop-2-enyl)morpholine (10 g, 27.7 mmol) was introduced under a stream of dry nitrogen followed by AlCl$_3$ (5 mol %, 0.18 g, 1.4 mmol). The resulting suspension was stirred at room temperature for 16 h or at 80° C. for 2 h. The reaction was subsequently quenched by addition of water (10 mL) at 4° C. The lower fluorochemical phase was separated and dried over Na$_2$SO$_4$. Filtration to remove the desiccating agent yielded 9.3 g of clear liquid product. Analysis of the product by GC-FID revealed 99.9% conversion of the terminal allylic double bond to internal double bond and a final E:Z ratio of 97:3 for the 1-propenylamine product produced. The GC assignments of E and Z isomers were confirmed by GC-MS and $^{19}$F NMR spectroscopy.

Example 7

Isomerization of 1,1,2,3,3-pentafluoro-N,N-bis(trifluoromethyl)prop-2-en-1-amine to (E)-1,2,3,3,3-pentafluoro-N,N-bis(trifluoromethyl)prop-1-en-1-amine with AlCl$_3$

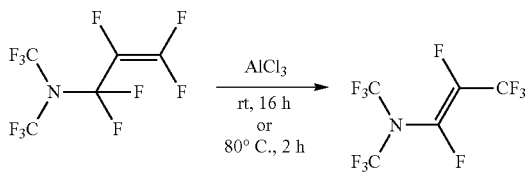

In a 25-mL two-neck round bottom flask equipped with magnetic stir bar, rubber septum, and inlet adapter connected via tubing to a Schlenk line, 1,1,2,3,3-pentafluoro-N,N-bis(trifluoromethyl)prop-2-en-1-amine (10 g, 35.3 mmol) was introduced under a stream of dry nitrogen followed by AlCl$_3$ (5 mol %, 0.23 g, 1.76 mmol). The resulting suspension was stirred at room temperature for 16 h. For high temperature isomerization (i.e.; 80° C.), the substrate and catalyst were placed in a glass pressure vessel and heated for 2 h. The reaction was subsequently quenched by addition of water (10 mL) at 4° C. The lower fluorochemical phase was separated and dried over Na$_2$SO$_4$. Filtration to remove the desiccating agent yielded 9.1 g of clear liquid product. Analysis of the product by GC-FID revealed 99.9% conversion of the terminal allylic double bond to internal double bond and a final E:Z ratio of 97:3 for the 1-propenylamine product produced. The GC assignments of E and Z isomers were confirmed by GC-MS and $^{19}$F NMR spectroscopy.

Example 8

Isomerization of 2,2,3,3,5,5,6,6-octafluoro-4-(1,1,2,3,3-pentafluoroprop-2-enyl)morpholine to (E)-2,2,3,3,5,5,6,6-octafluoro-4-(1,2,3,3,3-pentafluoroprop-1-enyl)morpholine with SbCl$_5$

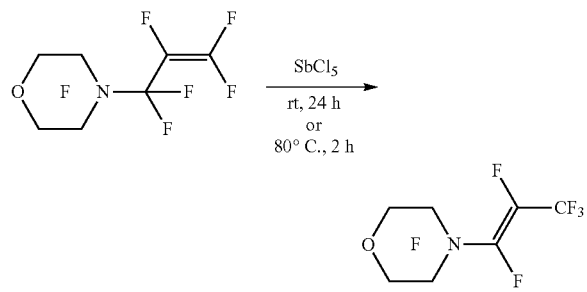

In a 25-mL two-neck round bottom flask equipped with magnetic stir bar, thermocouple, and inlet adapter connected via tubing to a Schlenk line, 2,2,3,3,5,5,6,6-octafluoro-4-(1,1,2,3,3-pentafluoroprop-2-enyl)morpholine (10 g, 27.7 mmol) was introduced under a stream of dry nitrogen followed by SbCl$_5$ (5 mol %, 0.42 g, 1.4 mmol). The resulting solution was stirred at room temperature for 24 h or at 80° C. for 2 h. The reaction was subsequently quenched by addition of water (10 mL) at 4° C. The lower fluorochemical phase was separated and dried over Na$_2$SO$_4$. Filtration to remove the desiccating agent yielded 9.5 g of clear liquid product. Analysis of the product by GC-FID revealed 90% and 99.9% conversion at 25° C. and 80° C., respectively, of the terminal allylic double bond to internal double bond and a final E:Z ratio of 97:3 for the 1-propenylamine product produced in both cases. The GC assignments of E and Z isomers were confirmed by GC-MS and $^{19}$F NMR spectroscopy.

Example 9

Isomerization of 1,1,2,3,3-pentafluoro-N,N-bis(perfluoropropyl)prop-2-en-1-amine to (E)-1,2,3,3,3-pentafluoro-N,N-bis(perfluoropropyl)prop-1-en-1-amine with AlCl$_3$

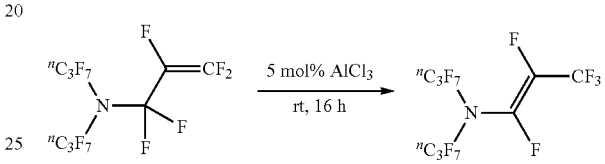

To an 8 mL vial equipped with a stir bar was charged AlCl$_3$ (28 mg, 21 mmol, 5.0 mol %) and 1,1,2,3,3-pentafluoro-N,N-bis(perfluoropropyl)prop-2-en-1-amine (2.0 g, 4.1 mmol). The resultant mixture was allowed to stir at room temperature for 16 h before filtering through a 0.45 μm PVDF syringe filter to give a colorless liquid filtrate (1.95 g). GC analysis of the filtrate confirmed 99% conversion of the starting material and an E:Z-1-aminopropene ratio of 98:2. GC analysis also revealed that at least 96.5% of the filtrate comprised the expected isomerization products, E- and Z-1-aminopropene. All structures were confirmed by GC-MS analysis and $^{19}$F NMR spectroscopy.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows. All references cited in this disclosure are herein incorporated by reference in their entirety.

What is claimed is:

1. A method of making a composition, the method comprising:
contacting a perfluorinated allylamine of general formula (2) with an active isomerization catalyst;

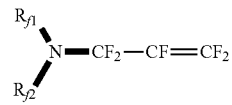

(2)

carrying out a selective catalytic isomerization to form a 1-propenylamine of general formula (1);

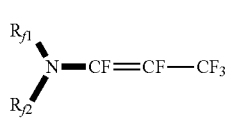
(1)

wherein each $R_{f1}$ and $R_{f2}$ comprises:
(i) independently a linear or branched perfluoroalkyl group having 1-8 carbon atoms and optionally comprises one or more catenated heteroatoms; or
(ii) bonded together to form a ring structure having 4-8 carbon atoms and that
optionally comprises one or more catenated heteroatoms, and
wherein the selectivity for formation of the E isomer of formula (1) is at least 60 wt. %, based on the total weight of the propenylamine in the composition.

2. A working fluid comprising a composition according to claim 1, wherein the composition is present in the working fluid at an amount of at least 25% by weight based on the total weight of the working fluid.

3. A method of transferring heat comprising:
providing a device; and
transferring heat to or from the device using a heat transfer fluid that the composition or working fluid according to claim 1.

* * * * *